United States Patent [19]

Remo et al.

[11] Patent Number: 5,142,144
[45] Date of Patent: Aug. 25, 1992

[54] METHODS AND MEANS FOR DETECTION OF DANGEROUS SUBSTANCES

[75] Inventors: John L. Remo, St. James; Robert Turner, Coram, both of N.Y.

[73] Assignee: Quantametrics Inc., St. James, N.Y.

[21] Appl. No.: 547,751

[22] Filed: Jul. 2, 1990

[51] Int. Cl.⁵ .............................................. G01N 33/00
[52] U.S. Cl. ................... 250/288; 73/23.35; 73/23.4
[58] Field of Search ............................. 73/23.35, 23.4; 250/379, 423 P, 288 A

[56] References Cited

U.S. PATENT DOCUMENTS

| | | | |
|---|---|---|---|
| 3,134,898 | 5/1964 | Burnall et al. ............... | 250/379 |
| 3,169,389 | 2/1965 | Green et al. ................. | 73/23.35 |
| 3,169,832 | 2/1965 | Galloway et al. ........... | 73/23.35 |
| 4,398,152 | 8/1983 | Leveson ..................... | 250/423 P |
| 4,413,185 | 11/1983 | Leveson ..................... | 250/423 P |

Primary Examiner—Hezron E. Williams
Assistant Examiner—Shu-Cheng Kau
Attorney, Agent, or Firm—Stanger, Michaelson, Spivak & Wallace

[57] ABSTRACT

The presence of dangerous substances such as cocaine is detected by atmospheric samples that include the residues (such as ether) of the manufacture of the suspected substances into a gas chromatograph to remove substances other than the residues and thereafter drawing them into a proportional counter chamber having a high voltage and a signal wire. A laser passes light capable of exciting the suspected residues through the proportional counter to produce ionization and generate a photoelectron. The signal wire passes this to an analyzer which indicates the presence of the suspected residues.

15 Claims, 3 Drawing Sheets

| STATE | POINT GROUP | $T_0$ | VIBRATIONAL FREQUENCIES $\nu_1$ $\nu_2$ $\nu_3$ $\nu_4$ $\nu_5$ $\nu_6$ | ROTATIONAL CONSTANTS $A_0$ $B_0$ $C_0$ $r_0(\text{Å})$ $\alpha$ | OB- SERVED TRANSI- TIONS | REFER- ENCES | REMARKS |
|---|---|---|---|---|---|---|---|
| $C_2H_5OH$ | | | see (539), (946) and (480) | I.P. = 10.50 eV | From Photoionization Data of (1273) | | |
| $(CH_3)_2O$ | | | I.P. = 9.96 eV | From Photoionization Experiments (1273) Obtains 10.00 eV | | | |
| | | | Rydberg series joining on to $\bar{E}$: $\nu = 80330 - R/(n - 0.02)^2$, $n = 3, 4, 5, 6$ | | | (511) | First members have progressions in $\nu$ |
| $\bar{F}$ | | 71170 | $\nu_7 = (410)$ | | $\bar{F} \leftarrow \bar{X}$ 1405–1381 Å | (511) | Diffuse bands |
| $\bar{E}$ | | 68120 | $\nu_7 = (400)$ | | $\bar{E} \leftarrow \bar{X}$ 1468–1442 Å | (511) | Diffuse bands |
| $\bar{D}$ | | 61390 | $\nu_7 = 410$ | | $\bar{D} \leftarrow \bar{X}$ 1630–1595 Å | (511) | Diffuse bands |
| $\bar{C}$ | | 58820 | $\nu_7 = 340$ | | $\bar{C} \leftarrow \bar{X}$ 1709–1680 Å | (511)(481) | Diffuse bands |
| $\bar{B}$ | | 53140 | $\nu_7 = 340$ | | $\bar{B} \leftarrow \bar{X}$ 1880–1840 Å | (511)(481) | Diffuse bands |
| $\bar{A}$ | | (42500) | continuum with rapidly increasing intensity towards shorter wavelengths | | $\bar{A} \leftarrow \bar{X}$ 2350–1980 Å | (481)(1204) | |
| $\tilde{X}^1\tilde{A}_1$ | $C_2$ | 0 | 2997 2821 1448 1242 1053 929 | 1.29384 0.33545 0.29644 $r(CO)=1.410$ $\angle COC=111.7°$ $r(CH)=1.096$ $\angle HCH=108.5°$ | infrared, Raman and microwave sp. | (23)(1194) (124) | |

$\nu_7$ to $\nu_{21}$ = 413, 2889, 1456, 1291, 160, 2889, 1440, 1291, 270, 2889, 1440, 1291, 1291, 1122 CH distances and angles are averages. The actual $CH_3$ groups are slightly asymmetric; see (124)

FIGURE 4

METHODS AND MEANS FOR DETECTION OF DANGEROUS SUBSTANCES

BACKGROUND OF THE INVENTION

This invention relates to methods and means for detecting the presence of dangerous substances, and particularly to the detection of the presence of illegal drugs such as cocaine.

Current methods of detecting the presence of illegal drugs and their manufacturing facilities are inadequate and insufficiently sensitive for authorities to find and deal with such drugs. The techniques are also incapable of discriminating between permissible and illegal substances.

OBJECTS AND SUMMARY OF THE INVENTION

An object of the invention is to improve methods and means for detecting dangerous substances.

According to a feature of the invention, this object is attained by using a gas chromatograph to separate a residual solvent used in the manufacture of the dangerous substance from background organic components in atmospheric free air, and using a laser operating at a wavelength suitable to photoionize electronic states in the gas molecules of the separated residual solvent, and with an analyzer determining the presence of the gas molecules of the separated residual solvent.

According to other features of the invention, the gas solvent is ether, the laser is a KrCl excimer laser, and the wavelength is 222 nm.

These and other features of the invention are pointed out in the claims. Other objects and advantages of the invention will become evident from the following detailed description when read in light of the accompanying drawings.

BRIEF DESCRIPTION OF THE DRAWINGS

FIG. 4 is a table showing characteristics of the ether molecule.

DETAILED DESCRIPTION OF PREFERRED EMBODIMENTS

Figure 1:
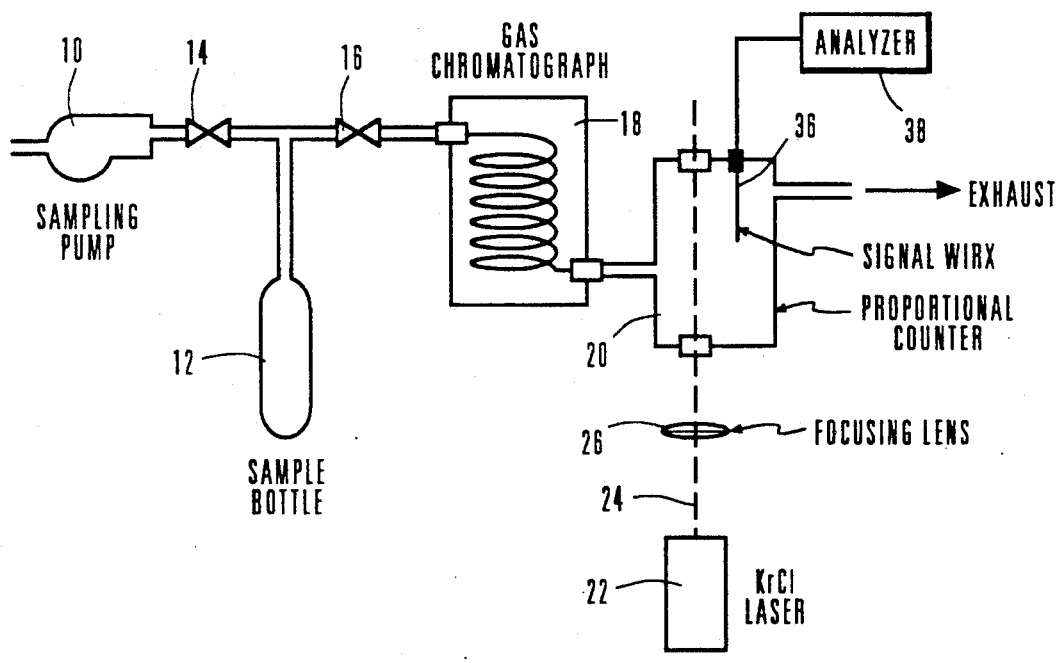
FIG. 1 is a schematic illustration of the device embodying features of the invention.

In FIG. 1, a sampling pump 10 draws atmospheric air near a suspected source of cocaine into a sampling bottle through a valve 14. A valve 16 transmits the content of the bottle 12 or pump 10 to a gas chromatograph 18 which separates the background organic components such as alcohol, methanol, etc. from the ether that constitutes the cocaine manufacturing residue. The gas chromatograph 18 transmits the ether to a proportional counter 20 (or optical processing cell 20). A KrCl laser 22 operating at a UV excitation of 222 nm passes laser light 24 through a focusing lens 26 and through the proportional counter 20. A signal wire 36 senses the ionization in the counter 20 and provides the resulting data to an analyzer 38.

Figure 2:
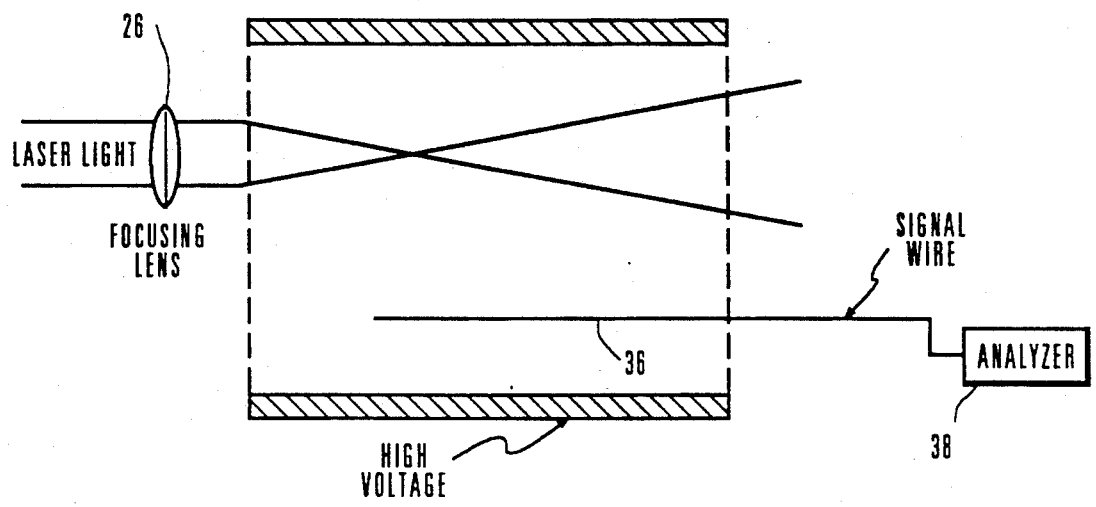
FIGS. 2 and 3 are schematic illustrations showing details of portions of FIG. 1.
Figure 3:
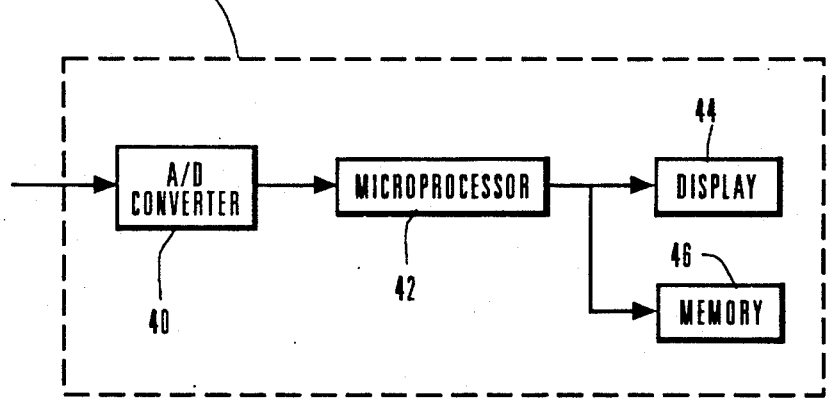

FIG. 2 illustrates details of the counter 20, the analyzer 38 and the focusing lens 26. FIG. 3 illustrates details of the analyzer 38 which includes an A/D converter 40, a microprocessor 42, a display 44, and a memory 46.

In operation, the sampling pump 10 draws atmospheric air from the neighborhood of suspected sources of cocaine into the sample bottle 12 through the valve 14, and the valve 16 passes the resulting gases to the gas chromatograph 18. The latter separates background organic components such as alcohol, methanol, etc. from the ether which is associated with the manufacture of cocaine. The resulting ether sample passes to the proportional counter 20. The KrCl excimer laser 22 passes a beam 24 through a focusing lens 26 into the proportional counter where the laser beam 24 photoionizes the electronic state in the ether molecule by resonantly enhanced two photon ionization.

This may be shown by considering Excitation energy $= 1.24 \times 10^{-6}$ eV / wavelength in m where the UV wavelength is $220 \times 10^{-9}$. Because the photon energy of 5.6 eV is greater than one half of the ether ionization potential shown in FIG. 4, it will take only two photons to exceed the ether ionization potential and generate a photoelectron which will be detected by the proportional counter.

The table of FIG. 4 appears in the publication of Gerhard Herzberg, *Electronic Spectra of Polyatomic Materials*. 651, table 79, Van Nostrand N.Y., 1966. See also A. Beiser. *Concepts of Modern Physics* 4 ed, Ch. 2, 1987.

The multiphoton ionization technique is extremely sensitive and capable of single atom detection as set forth in R.E. Turner et al, *The Multiphoton Ionization Spectra of Pyridine and Pyranzine*. Chem. Phys., 28. 47, 1978. Electrons generated from the photoionized (electronic state) ether, $C_4H_{10}O$, and collected by the proportional counter provide a pulse height signal. The analog digital converter 40 in the analyzer 38 of FIG. 2 converts the pulse height signal to digital values. The pulse height of the signal is directly proportional to the quantity of ether in the sample. A microprocessor 42 in the analyzer 38 then analyzes the signal and sends it to a display 44 and memory 46.

The invention offers the potential sensitivity to count very low levels of ether molecules, less than 1 part per billion. Hence, the energy required from a power supply for the system in FIG. 1 is small enough to permit extended field use. A device according to the invention is more sensitive than conventional gas chromatographic detectors.

The invention employs a very low power (1 mw) KrCl excimer laser 22 and a gas chromatograph 18 with packed columns. The small size of the components and simplicity of operation of these devices allows the entire system to be packaged into a module the size of carry-on luggage. The simplicity and availability of components assure a convenient inexpensive unit.

According to the invention the laser 22 may have a power from anywhere from 0.5 to 20 mw although the preferred value for easy transportation is 1 mw.

As stated, the invention affords a compact and lightweight directed energy device to detect ultra-low levels of residual solvents associated with the refinement of illegal drugs such as cocaine. While the described method and means concern the solvents associated with the manufacture of cocaine in particular, the invention may be embodied to detect other illegal, and/or dangerous substances. The directed energy instrument of the invention is lightweight, portable, reliable and inexpensive, is usable for inspecting baggage at customs and sampling the air in an aircraft, ships' cargo hold or other storage area. Additional applications with only minor modification of the disclosed embodiment allow the remote sampling of airborne solvents and other components associated with illegal drug refining. The extremely simple and rugged design of this instrument combined with the small power supply required for operation will assure the effective field use by personnel with only a minimal amount of training. Also, it would be extremely difficult to defeat the sensitivity for most tactical situations.

The device and method of the invention assure remote sensing and sampling of cocaine residues with a very sensitive technique for detecting ultra-low levels of residual solvents used in the manufacture of cocaine. However, these sensitive detection methods and means are also discriminating and selectively exclude unwanted chemical residues in favor of enhancing the suspected (residual) substance.

The invention utilizes a very low power (power output at 1 mw), rugged, inexpensive, and small KrCl excimer laser operating at 222 nm to irradiate and photoionize electronic states in ether gas molecules which have been separated from (atmospheric) free air flow samples and drawn into the proportional counter chamber cell 20. The gas chromatograph 18 separates the background organic components such as alcohol, methanol, etc. from the ether such that at the time of UV excitation at 222 nm the ether sample will be present in the optical sampling cell i.e. the proportional counter 20 of FIGS. 1 and 2.

The method and means of the invention are sensitive to the presence of ether because the 222 nm UV radiation from the KrCl laser photoionizes the electronic state in the ether molecule by resonantly enhanced two photon ionization.

The separation procedures used by the gas chromatograph are based on gas elusion times using gas chromatograph columns and packing materials in the form of molecular sieves.

The proportional counter chamber 20 is a form of voltage break down chamber.

While embodiments of the invention have been described in detailed, it will be evident to those skilled in the art that the invention may be embodied otherwise without departing from its spirit and scope.

What is claimed is:

1. A method for detecting the presence of dangerous substances, comprising:
   separating residues from the manufacture of the dangerous substances from atmospheric samples by means of a gas chromatograph;
   passing the suspected residues into a proportional counter;
   passing a laser beam having a wavelength capable of exciting the suspected residues; and
   measuring the ionization due to excitation of the residues;
   the step of passing a laser beam including passing a laser tuned to a frequency to produce resonantly enhanced multi-photon ionization.

2. A method for detecting the presence of dangerous substances, comprising:
   separating residues from the manufacture of the dangerous substances from atmospheric samples by means of a gas chromatograph;
   passing the suspected residues into a proportional counter;
   passing a laser beam having a wavelength capable of exciting the suspected residues; and
   measuring the ionization due to excitation of the residues;
   the step of passing a laser beam including passing a laser beam tuned to a frequency and at a power level to produce resonantly enhanced multi-photon ionization.

3. A method for detecting the presence of dangerous substance, comprising:
   separating residues from the manufacture of the dangerous substances from atmospheric samples by means of a gas chromatograph;
   passing the suspected residues into a proportional counter;
   passing a laser beam having a wavelength capable of exciting the suspected residues; and
   measuring the ionization due to excitation of the residues;
   the step of passing a laser beam including passing a laser beam having a power level smaller than that needed to exceed the ionization potential of the suspected residues.

4. A method for detecting the presence of dangerous substances, comprising:
   separating residues form the manufacture of the dangerous substances from atmospheric samples by means of a gas chromatograph;
   passing the suspected residues into a proportional counter;
   passing a laser beam having a wavelength capable of exciting the suspected residues;
   measuring the ionization due to excitation of the residues;
   the step of passing a laser beam including passing a laser beam having a power level smaller than that needed to exceed the ionization potential and having a frequency to produce resonantly enhanced multi-photon ionization.

5. An apparatus for detecting the presence of dangerous substances, comprising:
   a gas chromatograph for separating residues of the manufacture of the dangerous substances from other substances;
   a voltage breakdown chamber for holding gases and coupled to the gas chromatograph for receiving the suspected residues;
   a laser aligned with said chamber for passing a laser beam at a frequency capable of peak excitation of the suspected residues in said chamber; and
   means for responding to the break down in said chamber;
   said laser having a frequency to produce resonantly enhanced multi-photon ionization.

6. An apparatus as in claim 5 wherein said laser has a frequency and a power level to produce resonantly enhanced multi-photon ionization.

7. An apparatus as in claim 5 wherein the laser has a power level smaller than that needed to exceed the ionization potential of the residues.

8. An apparatus as in claim 5 wherein the laser has a power level smaller than that needed to exceed the ionization potential and a frequency to produce resonantly enhanced multi-photon ionization.

9. A method for detecting the presence of dangerous substances, comprising:
   separating residues from the manufacture of the dangerous substances from atmospheric samples by means of a gas chromatograph;

passing the suspected residues into the proportional counter;

passing a laser beam having a wavelength capable of exciting the suspected residues;

measuring the ionization due to excitation of the residues;

the step of passing the laser beam including passing a laser beam having a wavelength of $220 \times 10^{-9}$ meters with a laser having a power from 0.5 to 20 mw.

10. The method as in claim 9, wherein the laser power is 1 mw.

11. A method as in claim 9, wherein the excitation energy of the laser beam $1.24 \times 10^{-6}$ eV.

12. An apparatus for detecting the presence of dangerous substances, comprising:

a gas chromatograph for separating residues of the manufacture of the dangerous substances from other substances;

a voltage breakdown chamber for holding gases and coupled to the gas chromatograph for receiving the suspected residues;

a laser aligned with said chamber for passing a laser beam at a frequency capable of peak excitation of the suspected residues in said chamber; and means for responding to the break down in said chamber;

the laser being tuned to a wavelength of $220 \times 10^{-9}$ meters.

13. An apparatus as in claim 12, wherein said laser including means for producing a wavelength of $220 \times 10^{-9}$ meters at an excitation energy of $1.24 \times 10^{-6}$ eV.

14. An apparatus as in claim 13, wherein the laser has a power from 0.5 to 20 mw.

15. An apparatus as in claim 14, wherein the power is 1 mw.

* * * * *